United States Patent
Cohen et al.

[11] Patent Number: 6,042,376
[45] Date of Patent: Mar. 28, 2000

[54] NON-CIRCULAR ENDODONTIC INSTRUMENTS

[75] Inventors: Brett I. Cohen, Nanuet, N.Y.; Barry Musikant, Tenafly, N.J.

[73] Assignee: Essential Dental Systems, Inc., South Hackensack, N.J.

[21] Appl. No.: 09/258,931

[22] Filed: Mar. 1, 1999

[51] Int. Cl.[7] .................................................. A61C 5/02
[52] U.S. Cl. ............................................................ 433/102
[58] Field of Search .............................. 433/81, 102, 165, 433/166, 224

[56] References Cited

U.S. PATENT DOCUMENTS

| | | | |
|---|---|---|---|
| 444,383 | 1/1891 | Ivory | 433/102 |
| 1,067,015 | 7/1913 | Fowler | 433/102 |
| 1,527,845 | 2/1925 | Daniel | 433/102 |
| 4,260,379 | 4/1981 | Groves et al. | 433/102 |
| 4,634,378 | 1/1987 | Leonard | 433/102 |
| 4,661,061 | 4/1987 | Martin | 433/102 |
| 4,836,780 | 6/1989 | Buchanan | 433/102 |
| 4,934,934 | 6/1990 | Arpaio, Jr. et al. | 433/102 |
| 4,990,088 | 2/1991 | Weissman | 433/165 |
| 5,464,362 | 11/1995 | Heath et al. | 451/48 |
| 5,762,497 | 6/1998 | Heath | 433/102 |

Primary Examiner—John J. Wilson
Assistant Examiner—Melba Bumgarner
Attorney, Agent, or Firm—Wolff & Samson

[57] ABSTRACT

A non-circular endodontic instrument is provided for reduced stress to the tooth and to the cutting instrument during the removal of dentin from a root canal. The non-circular endodontic instrument includes at least one area of non-contact, i.e. one portion of the instrument does not contact and does not cut the dentin material. The non-contact area extends the length of the endodontic instrument, about a portion of the circumference of the instrument, and interrupts a generally circular cutting face of the instrument. This non-contact area reduces stress and provides a place for debris to gather during cutting so as to not interfere with the cutting face, and serves to direct the debris out of the root canal. The endodontic instrument can be D-shaped in cross-section, it could have circumferentially opposing non-contact areas and/or can be elliptical in cross-sectional shape.

15 Claims, 2 Drawing Sheets

NON-CIRCULAR ENDODONTIC INSTRUMENTS

BACKGROUND OF THE INVENTION

1. Field of the Invention

This invention relates to endodontic instruments having non-circular cross sections, and more specifically, to endodontic instruments for removing pulp tissue and widening root canals, which include cutting surfaces and non-contact surfaces spaced circumferentially about the instruments for decreasing stress and permitting debris to be directed away from the cutting surfaces of the instruments.

2. Related Art

When a diseased root canal (diseased pulp tissue) is found in the root canal of a patient's tooth, a dentist removes the pulp tissue in order to get access to the most apical end of the tooth where bacteria is normally found. Usually a series of files or reamers (hand instruments or rotary instruments) which have a circular cross section are used to both remove the pulp tissue and to widen the root canal. After the tissue is removed, irrigation solutions like Sodium Hypochlorite (NaOCl) are used to kill any remaining bacteria. Then the root canal is filled with gutta-percha and adhesive and sealed-off with such root canal preparations as the one sold by Essential Dental Systems, Inc. under the trademark EZ-Fill. Lastly, a crown could be fitted to the tooth.

The traditional endodontic instrument used to remove pulp tissue or dentin, in the root canal is circular in cross section. As the instrument engages the dentin, it creates a contact surface extending 360 degrees about the narrowest part of the canal. This complete circumferential contact creates resistance to the rotation of the instrument as it removes dentin. The resistance is transferred to both the instrument and the tooth in the form of stress. The greater the resistance, the greater the stress. Because the tooth is much thicker than the reamer or file, it has a minimum chance of distorting or fracturing. The reamer or file, which can be hand or rotary driven however, can easily distort by unwinding when engagement along the shank produces excessive torque generated by either hand or motor powered rotation. In fact, if rotation with excessive torque continues, the stainless steal reamer can unwind and then fracture. Ni—Ti (Nickel—Titanium) alloy instruments will generally fracture much more abruptly given the same amount torque because the Ni—Ti alloy is more flexible but failure can occur quickly and unpredictably.

One way to reduce the chances of excessive engagement is by using a sequence of ever thickening instruments that remove the dentin in a gradual fashion. In theory, each preceding reamer or file widens the canal enough to allow the incremental removal of dentin with the subsequent reamer or file never creating sufficient engagement for distortion during rotation. This technique is known as stepback because the wider reamers or files are also taken to a shallower depth to further minimize stress and distortion to the instrument.

Another technique employed in endodontics is called crown-down. It employs wider instruments first to open up the coronal aspects of the canal, and subsequentially thinner reamers and files are placed more and more apically. Both techniques attempt to reduce the amount of torque generated by limiting the degree of dentin engagement that the reamers and files encounter, to prevent excessive engagement of dentin which leads to distortion and potential fracture of the instruments.

However, the efforts by others in the past have not resulted in an endodontic instrument which reduces in stress in operation based on the geometry of the cutting surfaces of the instrument in relation to non-contact areas positioned circumferentially about the instrument.

Accordingly, what is desirable, and has not heretofore been developed, is the provision of an endodontic instrument which does not make full engagement with the dentin in a root canal during use so that stress is minimized and debris can be directed away from the cutting surfaces of the instrument.

Past efforts in this area, which have not been completely successful in providing stress-reducing endodontic instruments, include the following:

Heath, et al., U.S. Pat. No. 5,464,362, discloses a method for fabricating an endodontic instrument by a machining operation wherein a wire-like rod, composed of titanium alloy, is created with a high degree of flexibility, high resistance to torsional breakage, and sharp cutting edges along the working length. Said cutting edges having either a triangular or helical cross-section.

Weissman, U.S. Pat. No. 4,990,088, discloses a multi-functional dental tool having a first pointed end with a first shank cutting section and second, minor diameter shank section for reaming or drilling. Located immediately adjacent to the uppermost second section is a divergent counterbore section. Surrounding the maximum diameter of the counterbore section is an annular cleaner grinding surface and there above a top cutting section extending a relatively short distance above the grinding surface. The cutting portions of the tool include a lower drilling end, a counterbore portion, a larger routing section, and a top cutting section. The tool can be formed having a cross section of various regular polygons as desired, the apices of the polygons providing the cutting edges. The invention further discloses a combination dental tool wherein the shape of a lateral cross section of the first shank is a square or an equilateral polygon.

Arpaio, Jr. et al, U.S. Pat. No. 4,934,934, discloses a dental instrument adapted to be used as a dental file and reamer for removing dead or damaged tissue from the root canal of a tooth. The instrument is formed, having at least two helical flutes defining at least two continuous helical cutting edges. A helical peripheral end extends between the helical flutes at the periphery of the shank. The invention discloses an instrument having three or four continuous helical flutes and having helical cutting edges at the periphery of said working portion of said shank equally spaced about the circumference of said shank. The cross-sectional shape of one embodiment is triangular.

Martin, U.S. Pat. No. 4,661,061, discloses a dental instrument for performing root canal work. The end or working portion of the instrument is connected to the instrument shaft and is provided with four faces of like size, shape, and orientation, forming a generally square shaped cross-section. The four faces are joined to one another by four edges which meet at a point and are curved in an unbroken line toward each other, whereby when the canal is being rasped the debris is forced out of the canal away from the instrument end.

Leonard, U.S. Pat. No. 4,634,378, discloses a dental drill having a triple helicoidal flute and progressive pitch so that the free spaces between the cutting lips increase progressively as they move away from the top of the drill towards the shank. The flutes have cutting lips along peripheral edges thereof for drilling dental canals, and triple flutes at each cross-section of the drill.

Groves, et al., U.S. Pat. No. 4,260,379, discloses an endodontic instrument, whereby the file or reamer portion is manufactured by twisting an elongated tapered parallelogram ground bar. The resulting twisted configuration provides a file with a major diameter approximately corresponding to the long diagonal of the parallelogram and a minor diameter corresponding to the short diagonal of the parallelogram. The spiral edges defining the large diameter sections provide the cutting edges whereas the second set of alternating edges defining the reduced diameter sections provide a retaining and debris removal function during operation of the instrument. The result is an endodontic instrument with increased strength and stiffness compared to traditional endodontic instruments.

Daniel, U.S. Pat. No. 1,527,845, discloses an improved toothpick with a finger grip element of compressible material anchored to the stock by an attached wired element. The toothpick has a flattened end which can be used as a scraper.

Fowler, U.S. Pat. No. 1,067,015, discloses a dental broach which is constructed of flexible steel in order to serve as a nerve extractor and reamer, whereby such construction minimizes the risk of the broach binding or breaking in a root canal. The broach consists essentially of a round, spring-tempered wire. The broach is flattened at one end to form a generally rectangular cross-section, and placed in a suitable holder and by any suitable means turned or rotated to twist the flattened portion while forming a continuous double coil or spiral having continuous longitudinal reaming or cutting edges. This produces an extracting and reaming surface which has a screw-like action when the broach is rotated in a clockwise direction, thus adapting the broach for use in penetrating and cleaning out very small canals without the pressure usually required from conventional broaches.

None of the previous efforts, taken either alone or in combination, teach or suggest the provision of endodontic instrument having a non-circular cross section which includes one or more cutting surfaces and one or more non-contact areas positioned circumferentially about the instrument for reducing stress during the removal of dentin from a root canal, and for directing debris away from the cutting surfaces of the instrument.

OBJECTS AND SUMMARY OF THE INVENTION

It is a primary object of the present invention to provide an endodontic instrument that reduces stress during removal of dentin from a root canal.

It is another object of the present invention to provide an endodontic instrument having a non-circular cross section for reducing stress during removal of dentin material from a root canal.

It is an additional object of the present invention to provide an endodontic instrument having a non-contact area which does not make contact with a tooth and thus reduces stress, during the removal of dentin material from a root canal.

It is an additional object of the present invention to provide an endodontic instrument having a non-circular cross section which provides for a location for debris to collect away from cutting areas.

It is an additional object of the present invention to provide an endodontic instrument having a cutting face that extends only partially circumferentially about the endodontic instrument.

It is another object of the present invention to provide an endodontic instrument having a non-circular cross-section including a generally circular portion truncated by a flat area.

It is an additional object of the present invention to provide a non-circular endodontic instrument having an elliptical cross-section.

It is still even another object of the present invention to provide an endodontic instrument having two cutting areas on opposing sides of the instrument and two non-contact areas, positioned between the cutting areas, on opposing sides of the instrument.

These and other objects of the present invention are achieved by providing an endodontic instrument having a non-circular cross section. Preferably, the endodontic instrument of the present invention includes a non-contact area extending the length of the endodontic instrument which interrupts the generally circular cutting face of the instrument. The non-contact area does not make contact with the tooth during removal of dentin material and therefor decreases stress to the tooth and the endodontic instrument. The non-contact area also provides a place for debris to gather during cutting so as not to interfere with the cutting face, and serves to direct the debris out of the root canal.

In a preferred embodiment, the endodontic instrument of the present invention provides for a cutting surface or face that is generally circular in cross-section and extends about a portion the circumference of the instrument, but is interrupted, at one circumferential location, by a non-contact face, which extends the length of the instrument. The instrument can have more than one non-contact area and/or more than one cutting surface. The cutting surface includes helically extending cutting blades as is known in the art. The relative size of the cutting face (faces) versus the non-contact face (faces) can be varied as desired.

In another embodiment, the endodontic instrument comprises two generally curved cutting faces positioned in a circumferentially opposing relationship along the length of the instrument, and two non-contact faces positioned between the cutting faces.

In yet another embodiment, the instrument can be generally elliptical in cross-sectional shape.

Importantly, the present invention provides for reduced stress to the tooth and to the cutting instrument during the removal of dentin from a root canal, and does so by providing at least one area of non-contact, i.e. one portion of the instrument does not contact and does not cut the dentin material, but is recessed back from the general cross-sectional shape of the device to reduce stress to the tooth, maintain debris away from the cutting face of the device and to reduce instrument failure.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF THE INVENTION

Figure 1:
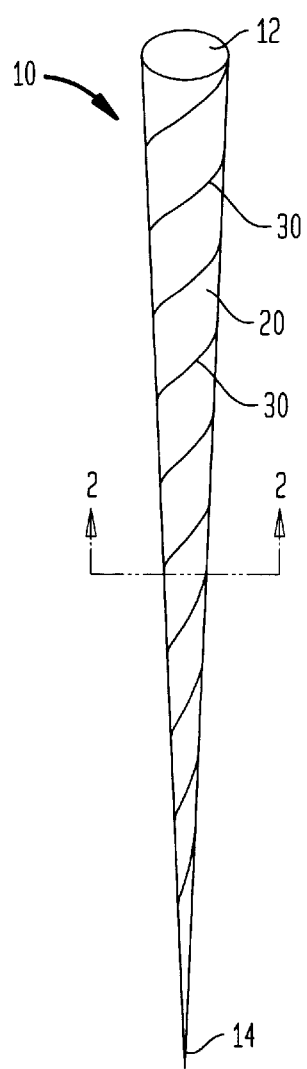
FIG. 1 is a perspective view of a prior art endodontic instrument.

Referring to FIG. 1, an endodontic instrument according to prior art is shown. The endodontic instrument is generally indicated at 10, and has a cutting surface 20 comprising cutting blades 30. The endodontic instrument 10 extends from an upper end 12 to a pointed lower end 14. Cutting blades 30 extend helically along the instrument 10 from the upper end 12 to the lower end 14.

Figure 2:
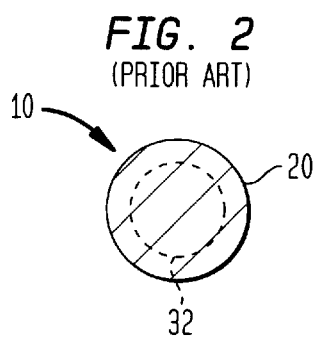
FIG. 2 is a cross-sectional view of the device shown in FIG. 1 taken along the lines 2—2.

Referring to FIG. 2, which is a cross-section of taken along the line 2—2 of FIG. 1, the endodontic instrument 10 is shown to include a cutting surface 20. The cutting blades 30 extend to a depth indicated by broken line 32. As can be seen, the cutting surface 20 extends entirely circumferentially around the instrument 10, and the instrument is generally circular in cross-section. In use, the instrument 10 engages the root canal at all aspects around the circumference of the instrument resulting in maximum stress to the tooth (not shown) and the instrument 10 during use.

Figure 3:
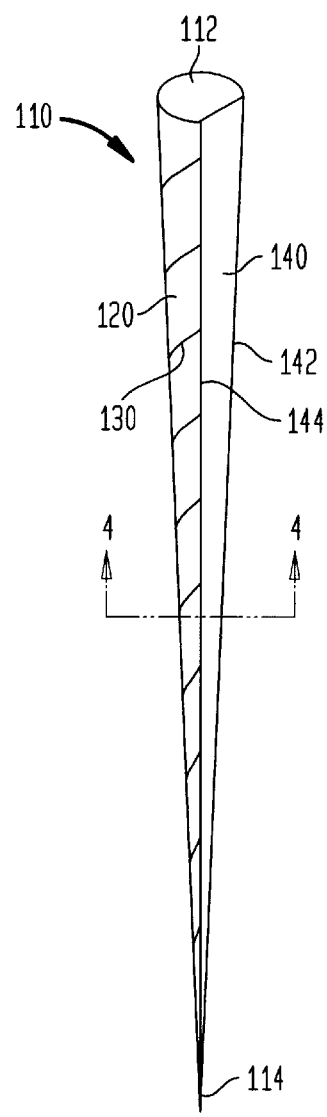
FIG. 3 is a perspective view of an endodontic instrument of the present invention having a cutting surface and a non-contact area.

Referring now to FIG. 3, an endodontic instrument according to the present invention is shown at 110. The instrument 110 includes an upper end 112 which tapers down along a length to a generally pointed lower end 114. The device includes a cutting surface 120 comprised of cutting blades 130 which extend helically along the cutting surface 120. The cutting surface 120 extends along the length of the instrument 110 about a portion of the circumference of the instrument 110. A non-contact area 140 also extends along the length of the instrument 110 about a portion of the circumference of the instrument 110.

Figure 4:
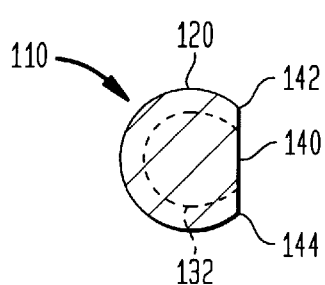
FIG. 4 is a cross-sectional view of the device shown in FIG. 3 taken along the line 4—4.

Referring to FIG. 4, which is a cross-sectional view of the instrument 110 taken along the line 4—4, it can be seen that the cutting blades 130 extend interiorly of the cutting surface 120 of the instrument 110 to depth indicated by broken line 132. FIG. 4 also clearly shows the non-contact area 140 defining a portion of the cross-section of the instrument 110, resulting in an overall non-circular cross-section for the instrument 110. The non-contact area 140 is interconnected with the cutting face 120 at juncture points 142 and 144. It can be seen that the instrument 110 is non-circular in cross-section, having generally, a D-shape.

In use, when the instrument 110 is inserted into a canal (not shown) and rotated, the cutting surface 120 with the cutting blades 130 engages the canal and removes dentin therefrom. The non-contact area 140 of instrument 110 does contact the canal area and thus reduces the stress caused by the engagement of the cutting face 120 with the canal. The non-contact area 140 also provides an area for debris to gather and be maintained out of the way of cutting face 120. Cutting is performed by the cutting blades 130 on cutting face 120. The resultant shape of the cut is circular in cross-section because the instrument 110 is axially rotated.

Figure 5:
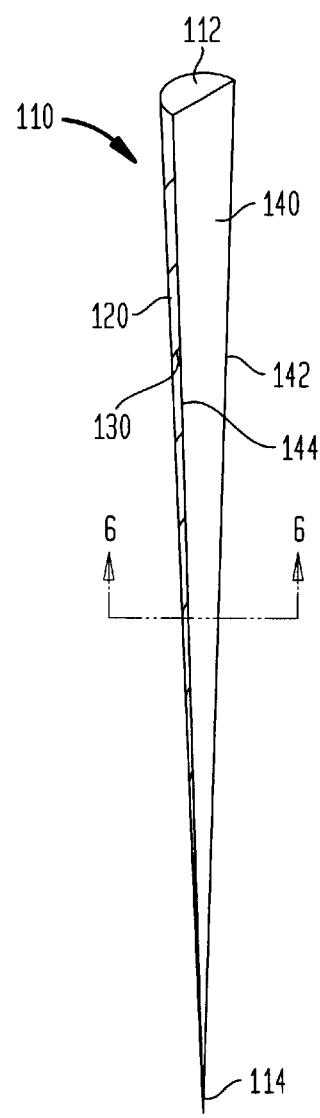
FIG. 5 is a view of the endodontic shown in FIG. 3 having a larger non-contact area.
Figure 6:
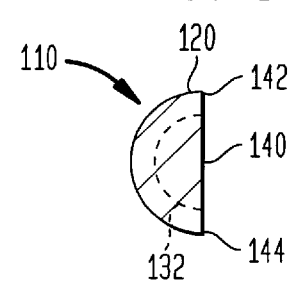
FIG. 6 is a cross-sectional view of the device shown in FIG. 5 taken along the line 6—6.

Referring to FIG. 5, a device similar to that of FIG. 3 is shown, except that the non-contact area 140 is of a greater dimension, and consequently the cutting face 120 is of a smaller dimension. Such an instrument 110 would serve to reduce stress to a larger extent based on the fact that the non-contact area is larger. FIG. 6 is a cross-sectional view of the instrument 110 shown in FIG. 5 taken along line 6—6. Accordingly, it should be pointed out that the relative sizes of the contact surfaces 120 and non-contact area 140 can be varied as desired to produce a desired result. Further, it should be pointed out that the cutting surface 120 can employ any known cutting means, including helical cutting blades 130, or any other known cutting means.

Figure 7:
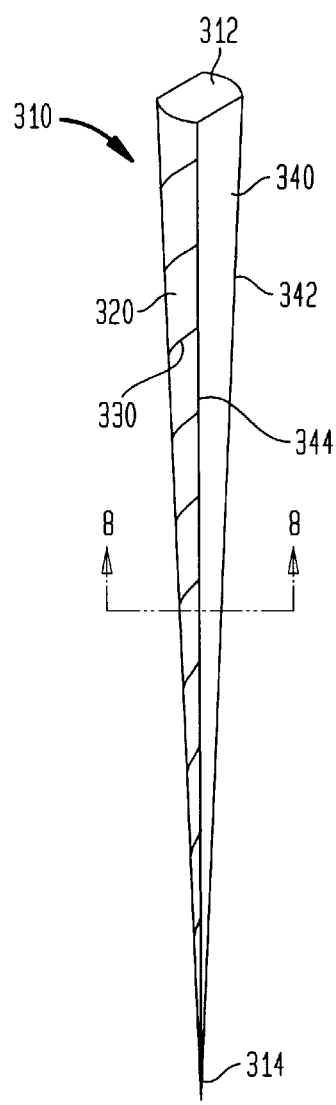
FIG. 7 is a perspective view of another embodiment of an endodontic instrument according to the present invention having two cutting surfaces and two non-contact areas.

Referring to FIG. 7, another embodiment of the endodontic instrument of the present invention is shown where the endodontic instrument, generally indicated at 310, includes two cutting faces 320 extending along the length of the instrument 310 at opposite circumferential sides of the device. The instrument 310 includes an upper end 312 which tapers down along a length to a generally pointed lower end 314. The cutting faces 320 include cutting blades 330 extending helically along the cutting faces 320. Two non-contact areas 340 comprising flat surfaces without cutting blades, extend along the length of the instrument 310 at opposite circumferential sides of device, interconnecting with the cutting faces at juncture edges 342 and 344.

Figure 8:
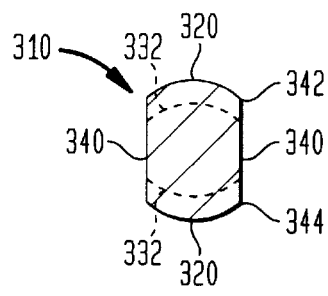
FIG. 8 is a cross-sectional view of the device shown in FIG. 7 taken along line 8—8.

This arrangement of cutting faces 320 and non-contact faces 340 of instrument 310 can be clearly seen in FIG. 8, which is a cross-sectional view along line 8—8, of the instrument 310 shown in FIG. 7. As can be seen, cutting faces 320 are found on opposite sides of the circumference of the instrument 310. Likewise, non-contact areas 340 are positioned on opposite sides of the circumference of the instrument 310. The non-contact areas 340 are positioned between the cutting surfaces 320. The cutting surfaces 320 have helical cutting blades 330, which extend inwardly from the surfaces of the cutting face 320 to broken line 332. Alternatively, the cutting face 320 can utilize any cutting means known in the art.

Importantly, the instrument 310 has a non-circular cross-section shape including cutting surfaces 320 and non-contact surfaces 340. The non-contact surfaces 340 serve to reduce stress during use, and also serve to maintain cut debris out of the way of cutting surfaces 320. It should be pointed out that other geometric arrangements of cutting surfaces and non-contact surfaces positioned along an endodontic instrument, resulting in an instrument having non-circular cross-section, are considered within the scope of the present invention.

Figure 9:
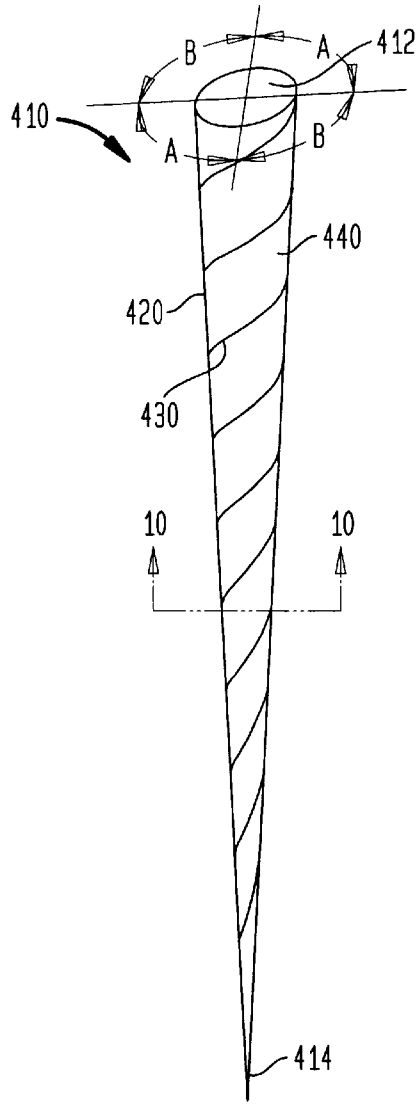
FIG. 9 is a perspective view of another embodiment of an endodontic instrument according to the present invention having an elliptical cross-sectional shape.
Figure 10:
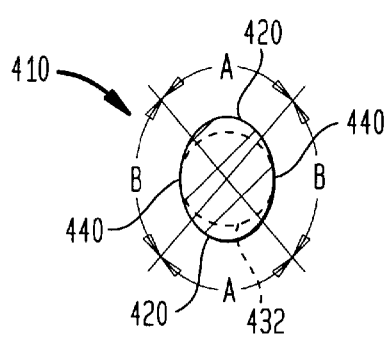
FIG. 10 is a cross-section view of the device of FIG. 9 taken along line 10—10.

Referring now to FIGS. 9 and 10, another embodiment of the instrument of the present invention is shown having an elliptical shape. The instrument, generally indicated at 410, includes an upper end 412 and a lower end 414 and a length tapering from the upper end 412 to lower end 414. The instrument 410 includes ends A and sides B. The end portions A comprise the cutting faces 420, and the long side portions B comprise the non-contact areas 440. Cutting blades 430 extend about the instrument 410. The cutting blades extend into the instrument to a depth shown by phantom line 432. As the endodontic instrument 410 is rotated, it will remove dentin in a circular cross-sectional shape, but during use, only the edge portions A comprising the cutting faces 420 will engage the canal and the long side areas B comprising non-contact areas 440 will not engage the canal, thereby reducing stress and directing debris away from the cutting faces 420. Again, the instrument is non-circular in cross-section. It should be noted that the specific cross-section geometry can be varied as desired in accordance with the present invention.

Having thus described the invention in detail, it is to be understood that the foregoing description is not intended to limit the spirit and scope thereof. What is desired to be protected by Letters Patent is set forth in the appended claims.

What is claimed is:

1. An endodontic instrument comprising:
   an upper end;
   a pointed lower end;
   a length extending from near the upper end to the pointed lower end, the length tapering from the upper end to the lower end;
   a non-circular circumference;
   a cutting surface extending along the length of the instrument about a first portion of the circumference; and
   a flat non-contact area extending uninterrupted along the length of the instrument to the pointed lower end about a second portion of the circumference.

2. The instrument of claim 1 wherein the circumferential shape of the cutting surface is generally circular.

3. The instrument of claim 2 wherein the cross-section of the instrument is D-shaped.

4. The instrument of claim 3 wherein the cutting surface includes cutting blades.

5. The instrument of claim 4 wherein the cutting blades helically extend along the cutting surface.

6. The instrument of claim 1 wherein the flat non-contact area has a taper corresponding to the taper of the length.

7. The instrument of claim 1 wherein the flat non-contact area extends to the center axis of the instrument.

8. An endodontic instrument comprising:
   an upper end;
   a pointed lower end;
   a length extending from near the upper end to the lower end and tapering therealong; and
   a non-circular circumferential cross-section including at least one flat non-contact area extending uninterrupted along the length to the pointed lower end.

9. The instrument of claim 7 wherein the cross-section comprises a generally circular portion, with cutting blades, and a flat portion interrupting the generally circular portion.

10. The instrument of claim 9 wherein the cross-section comprises opposing generally circular portions with cutting blades and opposing flat portions positioned between the generally circular portions.

11. A non-circular endodontic instrument comprising:
    a length tapering from near an upper end to a pointed lower end, the length having a non-circular circumferential cross-section;
    a cutting surface extending along the length about a portion of the circumferential cross-section, the cutting surface having helical cutting blades extending therealong;
    a flat non-contact area extending uninterrupted along the length to the pointed lower end about a portion of the circumferential cross-section;
    the cutting surface being generally circular in circumferential cross-section;
    the non-contact area being linear in circumferential cross-section;
    the instrument inserted into a root canal and rotated therein to remove dentin, the cutting surface contacting and removing dentin, the non-contact area positioned away from the edge of the root canal and providing an area for debris to accumulate away from the cutting surface.

12. The instrument of claim 11 wherein the cross-section of the instrument is D-shaped.

13. The instrument of claim 11 wherein the device further comprises a second cutting area and a second flat non-contact area.

14. The instrument of claim 13 wherein the second cutting surface positioned opposite the cutting surface about the circumferential cross-section.

15. The instrument of claim 14 wherein the second flat non-contact area is positioned opposite the flat non-contact area about the circumference.

* * * * *